(12) United States Patent
Shamim et al.

(10) Patent No.: US 10,702,153 B2
(45) Date of Patent: Jul. 7, 2020

(54) WOUND DRESSING WITH REUSABLE ELECTRONICS FOR WIRELESS MONITORING

(71) Applicant: KING ABDULLAH UNIVERSITY OF SCIENCE AND TECHNOLOGY, Thuwal (SA)

(72) Inventors: Atif Shamim, Thuwal (SA); Muhammad Fahad Farooqui, Thuwal (SA)

(73) Assignee: KING ABDULLAH UNIVERSITY OF SCIENCE AND TECHNOLOGY, Thuwal (SA)

(*) Notice: Subject to any disclaimer, the term of this patent is extended or adjusted under 35 U.S.C. 154(b) by 367 days.

(21) Appl. No.: 15/561,239

(22) PCT Filed: Apr. 15, 2016

(86) PCT No.: PCT/IB2016/052182
§ 371 (c)(1),
(2) Date: Sep. 25, 2017

(87) PCT Pub. No.: WO2016/166731
PCT Pub. Date: Oct. 20, 2016

(65) Prior Publication Data
US 2018/0055359 A1 Mar. 1, 2018

Related U.S. Application Data

(60) Provisional application No. 62/147,757, filed on Apr. 15, 2015.

(51) Int. Cl.
*A61B 5/00* (2006.01)
*A61F 13/00* (2006.01)
(Continued)

(52) U.S. Cl.
CPC .............. *A61B 5/0004* (2013.01); *A61B 5/00* (2013.01); *A61B 5/02042* (2013.01);
(Continued)

(58) Field of Classification Search
None
See application file for complete search history.

(56) References Cited

U.S. PATENT DOCUMENTS

| | | | |
|---|---|---|---|
| 6,356,243 B1 * | 3/2002 | Schneider | G06F 3/0231 343/765 |
| 2008/0171957 A1 * | 7/2008 | Connolly | A61B 5/0531 602/42 |

(Continued)

FOREIGN PATENT DOCUMENTS

| | | |
|---|---|---|
| WO | 2000079497 A1 | 12/2000 |
| WO | 2013026999 A1 | 2/2013 |

(Continued)

OTHER PUBLICATIONS

Sridhar, V., & Takahata, K. (2009). A hydrogel-based passive wireless sensor using a flex-circuit inductive transducer. Sensors and Actuators A: Physical, 155(1), 58-65. doi: 10.1016/j.sna.2009.08.010 (Year: 2009).*

(Continued)

*Primary Examiner* — Etsub D Berhanu
*Assistant Examiner* — James Stewart Stambaugh, III
(74) *Attorney, Agent, or Firm* — Patent Portfolio Builders PLLC

(57) ABSTRACT

A wound dressing device with reusable electronics for wireless monitoring and a method of making the same are provided. The device can be a smart device. In an embodiment, the device has a disposable portion including one or more sensors and a reusable portion including wireless electronics. The one or more sensors can be secured to a (Continued)

flexible substrate and can be printed by non-contact printing on the substrate. The disposable portion can be removably coupled to the one or more sensors. The device can include one or more sensors for wireless monitoring of a wound, a wound dressing, a body fluid exuded by the wound and/or wearer health.

20 Claims, 13 Drawing Sheets

(51) Int. Cl.
  *A61B 5/145* (2006.01)
  *A61B 5/02* (2006.01)
  *A61B 5/1477* (2006.01)
(52) U.S. Cl.
  CPC ........ *A61B 5/1477* (2013.01); *A61B 5/14539* (2013.01); *A61B 5/445* (2013.01); *A61B 5/6802* (2013.01); *A61F 13/00055* (2013.01); *A61B 5/14532* (2013.01); *A61B 2562/0214* (2013.01); *A61B 2562/125* (2013.01)

(56) References Cited

U.S. PATENT DOCUMENTS

| | | | | |
|---|---|---|---|---|
| 2008/0275327 | A1* | 11/2008 | Faarbaek | A61B 5/0002 600/382 |
| 2010/0326211 | A1* | 12/2010 | Stein | A61B 5/4528 73/862.636 |
| 2011/0012793 | A1* | 1/2011 | Amm | H01Q 1/243 343/702 |
| 2012/0214422 | A1* | 8/2012 | Shi | H04B 1/3838 455/67.11 |
| 2013/0120157 | A1 | 5/2013 | Geva | |
| 2013/0271278 | A1* | 10/2013 | Duesterhoft | A61B 5/002 340/539.12 |

FOREIGN PATENT DOCUMENTS

| | | |
|---|---|---|
| WO | 2014116816 A1 | 7/2014 |
| WO | 2015168720 A1 | 11/2015 |

OTHER PUBLICATIONS

First Examination Report in related GC Application No. GC 2016-31163, dated May 17, 2018 (References D1 and D2 previously provided in IDS filed Sep. 25, 2017).
Office Action in European Application No. 16 720 907.1 dated Mar. 26, 2019.
Communication pursuant to Article 94(3) EPC in corresponding/ related European Application No. 16720907.1, dated Jul. 16, 2019.
Ang, P.K., et al., "Solution-Gated Epitaxial Graphene as pH Sensor," Journal of the America Chemical Society, Oct. 14, 2008, vol. 130, pp. 14392-14393.
Cutting, K., "Wound Exudate: Composition and Functions," British Journal of Community Nursing, Feb. 2003, vol. 8 (9 Suppl), pp. 4-9.
Dharmarajan, T.S., et al., "Pressure Ulcers: Clinical Features and Management," Hospital Physician, Clinical Review Article, Mar. 2002, vol. 38, pp. 64-71.
Farrow, M.J., et al., "Developing a Real Time Sensing System to Monitor Bacteria in Wound Dressings," Biosensors, May 9, 2012, vol. 2, pp. 171-188.
Gist, S., et al., "Wound Care in the Geriatric Client," Clinical Interventions in Aging, Jun. 9, 2009, vol. 4, pp. 269-287.
Guinovart, T., et al., "Bandage-Based Wearable Potentiometric Sensor for Monitoring Wound Ph," Electroanalysis, Mar. 13, 2014, vol. 26, pp. 1345-1354.
International Search Report in related International Application No. PCT/IB2016/052182, dated Jun. 17, 2016.
Jung, D., et al., "pH-Sensing Characteristics of Multi-Walled Carbon Nanotube Sheet," Materials Letters, Oct. 29, 2013, vol. 116, pp. 57-60.
Lei, et al., "Simple Gaphene Chemiresistors as pH Sensors: Fabrication and Characterization," Measurement Science and Technology, Aug. 26, 2011, vol. 22, No. 10.
Li, Z et al., "Non-Invasive Transdermal Two-Dimensional Mapping of Cutaneous Oxygenation with a Rapid Drying Liquid Bandage," Biomedical Optics Express, Optical Society of America, Oct. 1, 2014, vol. 5.
McColl, D., et al., "Real-Time Monitoring of Moisture Levels in Wound Dressings In Vitro: An Experimental Study," International Journal of Surgery, Oct. 2007, vol. 5, pp. 316-322.
Mehmood, N., et al. "An Improved Flexible Telemetry System to Autonomously Monitor Sub-Bandage Pressure and Wound Moisture," Sensors, Nov. 18, 2014, vol. 14, pp. 21770-21790.
Nunan, R., et al., "Clinical Challenges of Chronic Wounds: Searching for an Optimal Animal Model to Recapitulate Their Complexity", The Company of Biologists Ltd, Disease Models & Mechanisms, Nov. 2014, vol. 7, pp. 1205-2313.
Schreml, S., et al., "The Impact of the pH Value on Skin Integrity and Cutaneous Wound Healing," Journal European Academy of Dermatology and Venereology, Aug. 23, 2009, vol. 24, pp. 373-378.
Sen, C.K., et al., "Human Skin Wounds: A Major and Snowballing Threat to Public Health and Economy," Wound Repair Regen., Nov. 1, 2009, vol. 17, pp. 763-771.
Swisher, S.L., et al., "Impedance Sensing Device Enables Early Detection of Pressure Ulcers in Vivo," Nature Communications, Mar. 17, 2015, vol. 6, pp. 6575-6585.
Winokur, E.S., et al., "A Wearable Cardiac Monitor for Long-Term Data Acquisition and Analysis," IEEE Trans. Biomedical Engineering, Jan. 2013, vol. 60, pp. 189-192.
Written Opinion of the International Searching Authority in related International Application No. PCT/IB2016/052182, dated Jun. 17, 2016.
Zheng, Y-L., et al., "An Armband Wearable Device for Overnight and Cuff-less Blood Pressure Measurement," IEEE Transactions on Biomedical Engineering, Apr. 18, 2014, vol. 61.

\* cited by examiner

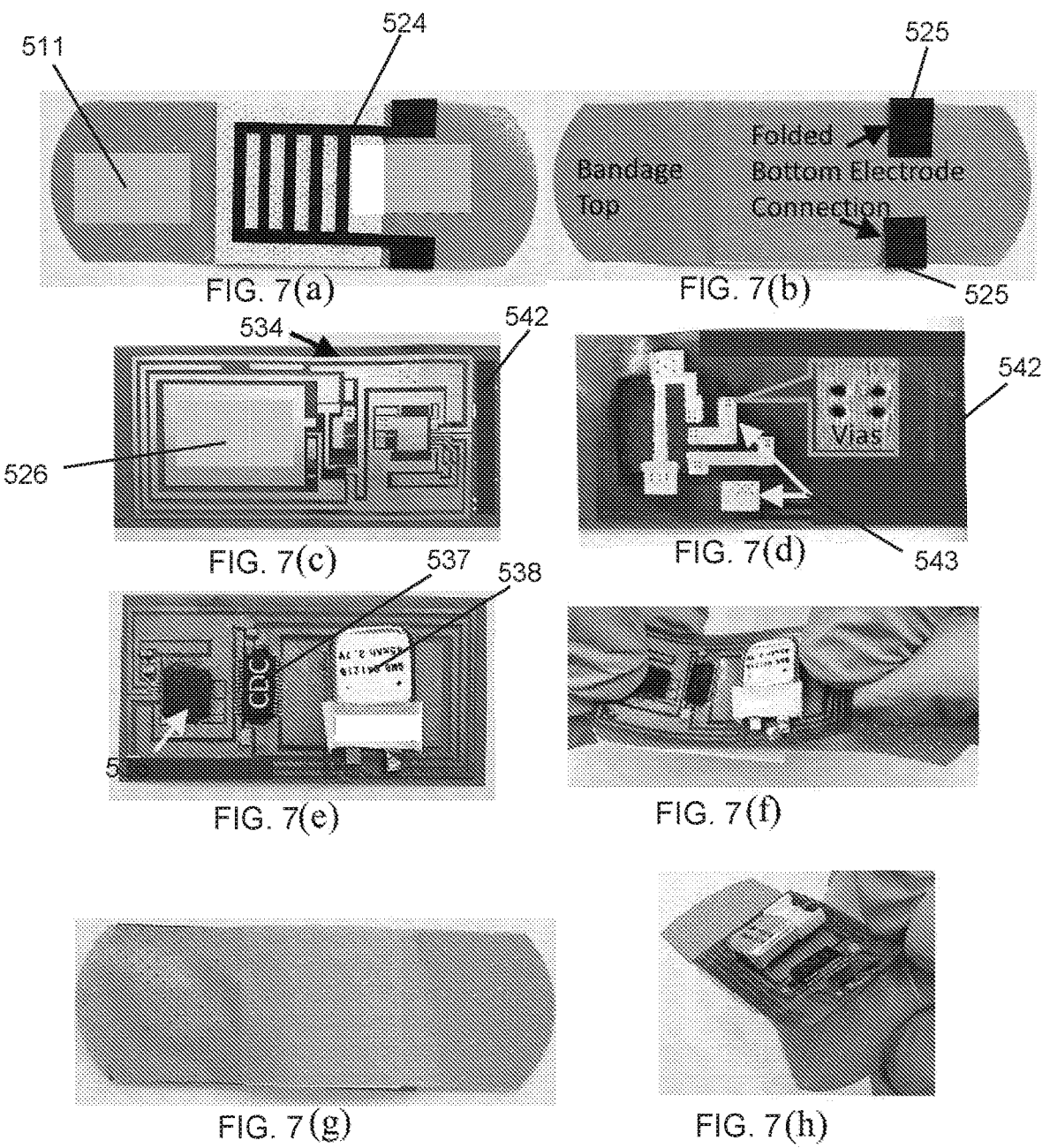

FIG. 8(a)
FIG. 8(b)
FIG. 8(c)
FIG. 8(d)
FIG. 8(e)
FIG. 8(f)
FIG. 8(g)
FIG. 8(h)
FIG. 8(i)
FIG. 8(j)
FIG. 8(k)
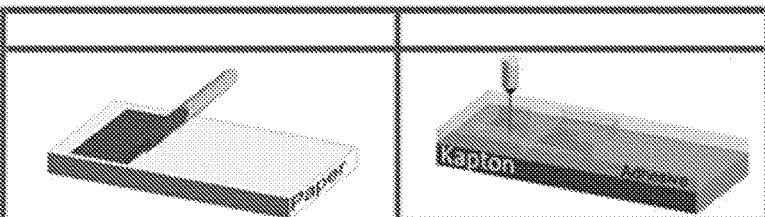
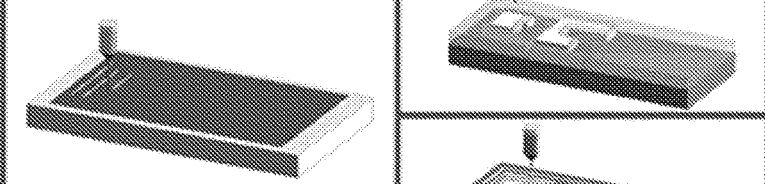
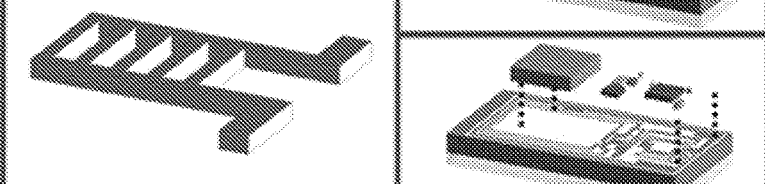
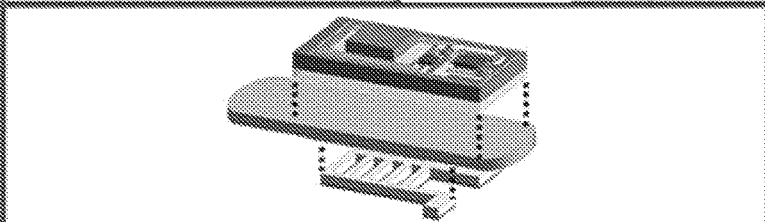
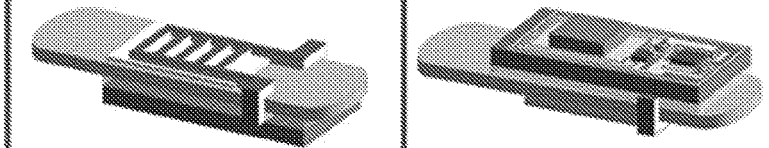
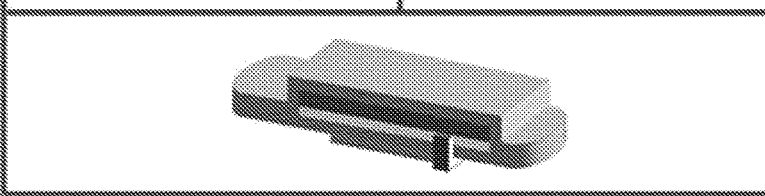

WOUND DRESSING WITH REUSABLE ELECTRONICS FOR WIRELESS MONITORING

CROSS-REFERENCE TO RELATED APPLICATIONS

This application claims priority to U.S. provisional application No. 62/147,757 filed on Apr. 15, 2015, having the title "WOUND DRESSING WITH REUSABLE ELECTRONICS FOR WIRELESS MONITORING", the entirety of which is incorporated herein by reference.

TECHNICAL FIELD

The present disclosure generally relates to wound dressings, in particular smart wound dressings having wireless monitoring of wound condition.

BACKGROUND

Monitoring of wounds under dressing is important for patients in an emergency ward in a hospital or for people who are wearing a bandage and busy in their day to day activities. At present, the change of dressing is decided upon one or more physical inspections. Similarly, monitoring of chronic wounds is critical especially for the elderly people as complications may occur if proper treatment is not provided in timely manner. Diabetes also alters the healing process. There is a need for a solution for monitoring wounds, wound condition, and wound dressings, in particular a low cost need therefor.

SUMMARY

The present disclosure addresses the aforementioned needs and the problem of wound monitoring by offering a low cost wearable solution that can collect and remotely send information about wound health, physiological conditions or parameters of a subject wearing the solution, as well as indicating a need to change the dressing. In this manner, patients can themselves monitor the condition of their wounds without requiring the physical presence of medical staff to periodically inspect the wound. This can also provide centralized monitoring of patients by medical staff, such as in a medical emergency department, that can result in reduction of the treatment cost associated with such cases.

In an aspect, the wearable solution comprises a wound dressing providing a wireless monitoring system. In one or more aspects, the wound dressing can provide a continuous monitoring system. The wearable solution can be realized through inkjet printing on a standard bandage. It can send collect and send information for the parameters such as irregular bleeding, variations in pH levels and/or blood sugar levels, and external pressure at wound site. The information can include early warnings for the parameters. In addition to the early warnings, our smart wound dressing concept can provide long term wound progression data to health care providers. In one or more aspects, the smart wound dressing can comprise a disposable portion which includes one or more sensors and a reusable portion including wireless electronics. The one or more sensors can be secured to a substrate and can be printed by non-contact printing on the substrate, such as by ink jet printing.

In an embodiment, the present disclosure provides a device for wireless monitoring of wounds and wound and/or subject health parameters. The device can include one or more sensors for wireless monitoring of a wound, a wound dressing and/or a body fluid exuded by the wound. The sensor can be an inkjet printed sensor, and related electronics can be provided. The sensor can provide capacitive and/or resistive sensing of wounds conditions that can be monitored wirelessly.

In an embodiment, the present disclosure provides a wound dressing comprising: a substrate; a sensor electrode, the sensor electrode mounted on an element for securing the sensor electrode to a side of the substrate; sensor electronics in communication with the sensor electrode, the sensor electronics including one or more components providing wireless communication of the sensor electrode to another device. In one or more aspects, the sensor electrode can be mounted on an element for securing the sensor electrode to the side of the substrate. The sensor electrode can be a printed sensor electrode. The sensor electrode can be a printed sensor electrode. The sensor electrode can be printed using an ink jet printer or at least a portion of the wireless electronics can be printed using an ink jet printer, or both are printed using an ink jet printer. The sensor electrode can be printed on adhesive tape, and the adhesive tape can be attached to the substrate, or the sensor electronics can be printed on adhesive tape, or both. The sensor electrode can be printed with silver nanoparticles based ink. The sensor electronics can be reusable in the assembly of another wound dressing system. The sensor electronics can be printed on adhesive tape. The sensor electronics can be printed using silver nanoparticles based ink. The sensor electrode can provide capacitive sensing of a wound condition or resistive sensing of a wound condition, or both, that can be monitored wirelessly. The disposable portion of the wound dressing system can include a capacitive sensor electrode or a resistive sensor electrode, or both. The wound dressing system can include a sensor electrode selected from the group consisting of a blood sensor electrode, a pH level sensing electrode, a blood glucose level sensing electrode, a pressure sensing electrode, and combinations thereof. The substrate can be a flexible substrate.

In an embodiment, a method of making the wound dressing system is provided. The method can comprise the steps of: providing a first substrate; printing one or more sensor electrodes on the first substrate; providing a second substrate; printing a circuit on the second substrate; coupling one or more of a transmitter, an antenna, a capacitance to digital converter, a battery or a processor to the circuit; and removably coupling the second substrate to the first substrate and coupling the sensor electrode on the first substrate to the circuit on the second substrate. In any one or more aspects of the method, the one or more sensor electrodes can include a capacitive sensor electrode and a resistive sensor electrode. A transmitter, an antenna, a processor and a capacitance to digital converter can be coupled to the circuit on the second substrate. The first and second substrates can be comprised of a flexible material.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIGS. 1(a) and 1(b) depict an embodiment of a wound dressing of the present disclosure, wherein FIG. 1(a) depicts an interdigitated sensor electrode at the bottom of the dressing and FIG. 1(b) depicts connection of a sensor electrode at the top of the dressing.

FIGS. 7(a)-(h) depict various fabrication and assembly steps of an embodiment of our present disclosure. FIG. 7(a) depicts bottom side view of a bandage showing a bottom side printed carbon based sensor electrode. FIG. 7(b) depicts a top side view of the bandage showing a folded connection for the bottom electrode. FIG. 7(c) depicts a top side view of an inkjet printed circuit board on Kapton tape. FIG. 7(d) depicts a bottom side view of the circuit board highlighting vias and pads for connecting the bottom sensor electrode. FIG. 7(e) depicts a detachable electronics portion comprising Kapton printed circuit tape after mounting of the components on the tape. FIG. 7(f) depicts the electronics being mounted on the bandage to form a smart bandage assembly. FIG. 7(g) depicts the smart bandage enclosed by a bandage strip acting as a cover package. FIG. 7(h) depicts the detachable electronics portion can be easily removed from the bandage after use.

FIGS. 8(a)-(k) depict a process for fabricating a system of the present disclosure. FIG. 8(a) depicts the carbon ink spreading on a paper substrate. Cutting of bottom electrode using laser, ad depicted in FIG. 8(b). FIG. 8(c) depicts separating the bottom sensor electrode. FIG. 8(d) depicts processing of bottom side of the Kapton tape 542. FIG. 8(e) depicts inkjet printing the bottom side of the circuit board. FIG. 8(f) depicts inkjet printing the top side of the circuit board. FIG. 8(g) depicts mounting of the circuit components using silver epoxy. FIG. 8(h) depicts mounting the bottom electrode and the integrated electronics on the disposable bandage strip 511. FIGS. 8(i) and (j) depict a bottom view of the smart bandage and a top view of the smart bandage, respectively. FIG. 8(k) depicts the addition of another disposable bandage strip on top of the detachable electronics for packaging purpose.

FIG. 9(a) depicts sensor capacitance measured for fixed volumes of sweat and blood (where sweat and blood are represented by equivalent properties fluids). The error bars show the variation in change of capacitance for different samples. FIG. 9(b) depicts sensor capacitance measured under the influence of external pressure on the bandage in the range of 5-100 mmHg.

FIGS. 11(a)-(b) depict measurements of an antenna for a system of the present disclosure in which FIG. 11(a) shows the reflection coefficient and FIG. 11(b) shows the active radiation patterns.

FIG. 15(a) shows the capacitance change under different bending radii and on body locations. An embodiment of our smart bandage (with exposed electronics) is shown worn on a wrist (FIG. 15(b)), an elbow (FIG. 15(c)), and on a shoulder (FIG. 15(d)).

DETAILED DESCRIPTION

Figure 1A:
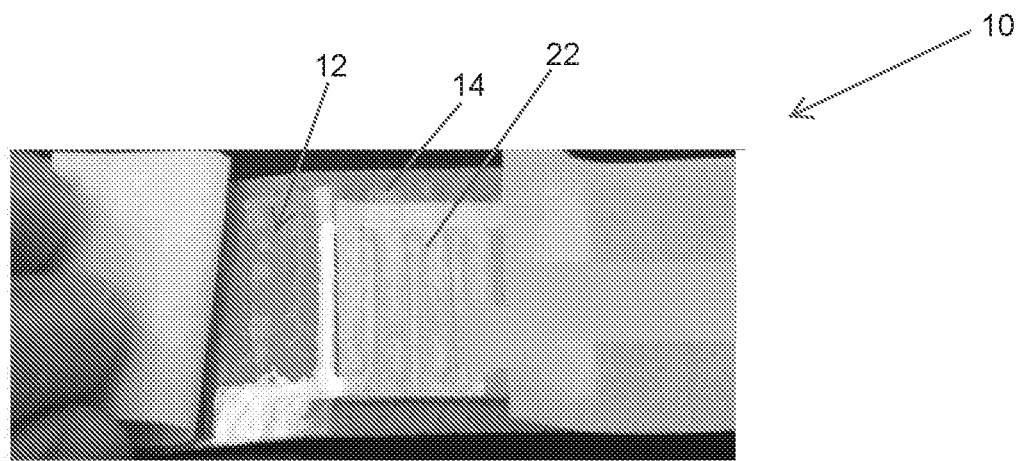

Described below are various embodiments of the present systems and methods for a wound dressing with reusable electronics for wireless monitoring. Although particular embodiments are described, those embodiments are mere exemplary implementations of the system and method. One skilled in the art will recognize other embodiments are possible. All such embodiments are intended to fall within the scope of this disclosure. Moreover, all references cited herein are intended to be and are hereby incorporated by reference into this disclosure as if fully set forth herein. While the disclosure will now be described in reference to the above drawings, there is no intent to limit it to the embodiment or embodiments disclosed herein. On the contrary, the intent is to cover all alternatives, modifications and equivalents included within the spirit and scope of the disclosure.

Discussion

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context dearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, synthetic inorganic chemistry, analytical chemistry, and the like, which are within the skill of the art. Such techniques are explained fully in the literature.

It is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

DESCRIPTION

Advances in wearable and flexible electronics along with the growth of wireless networking have created new paradigms of applications for smart living. One important application can be the development of advanced health monitoring systems that enable people to stay better informed about physiological changes in their bodies. Such systems can play a role in developing a healthy environment for better living and increasing the quality of life. Increase in population and rising cost of healthcare services have also created a growing demand to monitor a patient's health in personal environment outside of a hospital. Therefore, wearable sensors are being developed to monitor various physiological parameters of the human body. A number of sensors have been developed to monitor the vital signs of the human body including body temperature[1], heart rate[2], electrocardiogram[2,3] and blood pressure[4]. A few sensors have also been developed to monitor the brain activity by recording electroencephalogram[5].

Wound monitoring, in particular chronic wound monitoring, is one area of human health that has received relatively less attention from the research community. Chronic wounds present a significant challenge to modern health care providers as they affect more than 9 million people in the United States and Europe. The annual costs to treat chronic wounds exceed US$39 billion[6,7]. Wounds can be broadly classified into two categories, acute wounds and chronic wounds. Acute wounds follow an orderly healing process and close in a short period of time whereas chronic wounds do not follow an orderly healing process in a predictable amount of time. Chronic wounds either do not heal or heal very slowly and reoccur after healing. Wounds that do not heal within three months are termed chronic[8]. Usually, diabetic, obese and elderly people tend to suffer more from chronic wounds[9,10] and if treatment is not done in a timely manner, infections and complications can occur in these wounds.

Diagnosis and the treatment of chronic wounds are quite complex and pose a major challenge to health care staff. The reason is that the initial symptoms of a chronic wound are very subtle and it is hard to differentiate them from those of an acute wound[11]. It is therefore difficult to assess whether the healing process has been perturbed or not.

One of the major causes of disruption of the healing process is bacterial infection. An infection can result in the overgrowth of a newly formed capillary rich granulation tissue over the wound. This condition is termed as overgranulation and it can hamper the healing process. Overgranulation results in a protruding, friable flesh that is very sensitive and bleeds easily. As such, chronic wounds often show frequent and irregular bleeding[12]. Changes in pH values have also been related to the presence of infection. An infected wound shows slightly basic pH due to certain enzyme activities, bacterial colonization and formation of protein structures[13].

Chronic wounds can be classified into three major categories, namely diabetic foot ulcers, venous leg ulcers and pressure ulcers. These wounds vary in dimension, depth and the amount and composition of wound exudate. Pressure ulcers can develop if a part of the body is under sustained pressure for a longer period of time[14]. Such a situation usually occurs when a patient lies in the same position for a long time after any surgical operation in the intensive care unit (ICU) or if the patient has limited mobility. Obesity and inactivity due to age can increase the probability of pressure ulcers. The pressure causes reduced blood flow in the tissue that can lead to tissue death, and subsequently, an infection.

There is currently no commercially available wireless device to continuously monitor the wound healing process. Instead, patients rely on medical staff for physical inspection of the wound, which requires repeated trips to clinics or prolonged hospitalization. After surgical treatments, patients are manually repositioned every hour to relieve pressure in order to avoid the development of pressure ulcer. Few devices have been reported in the literature that monitor parameters related to the wound healing process. Those that have been reported include a bandage in solution form that can be painted onto the skin to form a thin film[15]. The film emits oxygen dependent phosphorescence that can be used to map the oxygen levels of the underlying skin tissue. A polyaniline (PANI) based potentiometric sensor realized on a bandage strip has been reported to detect the pH levels of the wound[16]. In another example, a flexible electrode array has been developed through the inkjet printing of gold nanoparticle on flexible polyethylene naphthalate to measure the impedance spectrum of the tissues for early detection of pressure ulcers[17]. Electrodes have been demonstrated to measure moisture levels[18] as well as bacteria[19] in wound dressings. A hydrogel based wireless sensor for pH monitoring of wounds has been fabricated[20].

These reports describe sensing of a single parameter related to the wound healing process. Also, the designs are not optimized for wearability and cost and some also require complex fabrication processes. None of them has an integrated wireless module, thus rendering them unsuitable for remote health monitoring applications. A close example is a wireless telemetry system that has been demonstrated to monitor the pressure and humidity levels in compression bandages[21]. However, the system dimensions are large as commercial sensors are used that are not integrated and are connected through wires.

Thus, wound healing is a complex process. Accurate diagnosis and treatment may require information about a number of factors that can affect wound healing. To this objective, we provide an attractive solution that is a low cost, wearable, compact, wireless, real-time wound monitoring system that can be worn by patients in everyday life. In one or more aspects, our wound dressing system or device can issue warnings (that can include early warnings) to the patients regarding any abnormality in the healing process, as well as wirelessly send the data recordings of multiple parameters related to the wound healing process to remote medical staff. In this way, health care providers can have access to the history of wound progression that can be important in the diagnosis and treatment process.

Adhesive bandages are most commonly used to protect wounds from the external environment and augment rapid healing. Here, we provide a novel complete wearable device and/or system to wirelessly monitor wounds (including chronic wounds) using a simple bandage strip. In various aspects, the device and system, termed a smart wound dressing or bandage, can comprise one or more inkjet printed sensors on a disposable bandage to monitor subject health parameters, such as bleeding, pH levels, blood sugar levels, and external pressure on a wound site. The one or more sensors can be smartly integrated on the bandage with wireless electronics that can be detached and reused on another bandage, thus providing disposability of the bandage strip in contact with the wound while providing a separable, reusable portion including a wireless module with wireless communication electronics.

The wearable smart wound dressing can alert the patient and the health care providers regarding any abnormality in the wound healing process through the integrated wireless module. Continuous monitoring also facilitates acquisition of long term wound progression data. In one or more aspects, the disposable portion of the wound dressing can include a bandage strip and one or more sensors and a removable, reusable portion including a circuit board and an antenna, that can be provided using low cost inkjet printing processes and flexible substrates which make our present smart wound dressing attractive in terms of wearability and cost.

The smart wound dressing system and device can be used to monitor any type of chronic wound regardless of its size as the sensor dimensions are scalable. In various aspects described in more detail below, we incorporate a commercial bandage strip to implement the system. Our smart wound dressing can be worn in daily life and can provide an attractive solution for remote health monitoring, and thus reducing the burden on health care services to meet the growing demands of the population.

In an embodiment, the present disclosure provides a device for wireless monitoring of wounds and/or subject health parameters (such as blood glucose levels). The device can include one or more sensors for wireless monitoring of a wound, a wound dressing and/or a body fluid exuded by the wound. The one or more sensors can be an inkjet printed sensors, and related electronics can be provided.

In one or more aspects the device can be a wound dressing comprising two parts. The first part can be a disposable dressing, for example a bandage, with one or more sensor electrodes. The disposable dressing can include a dressing substrate or wrap, for example a bandage strip, with the sensor electrode attached to the substrate. The sensor electrode can be a printed sensor electrode, for example printed by using an ink jet printer. The second part can be reusable electronics for the sensor.

Figure 1B:
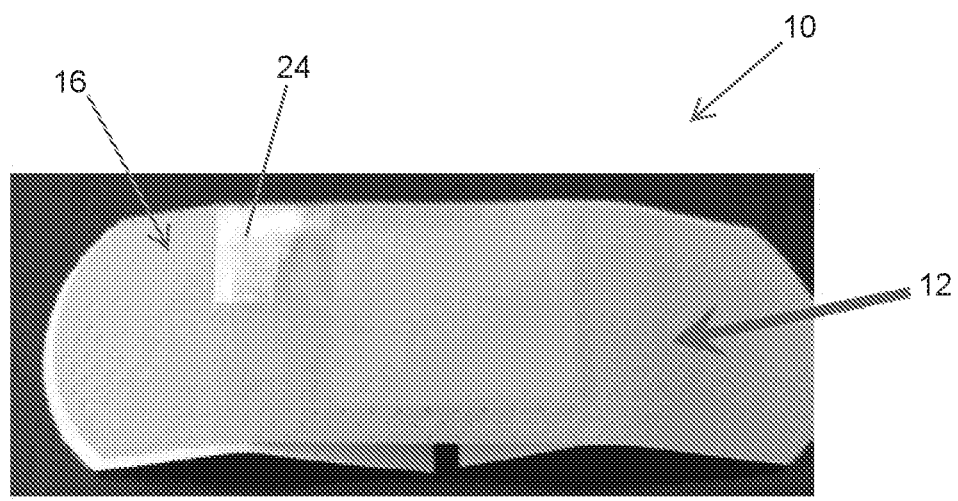
Figure 2A:
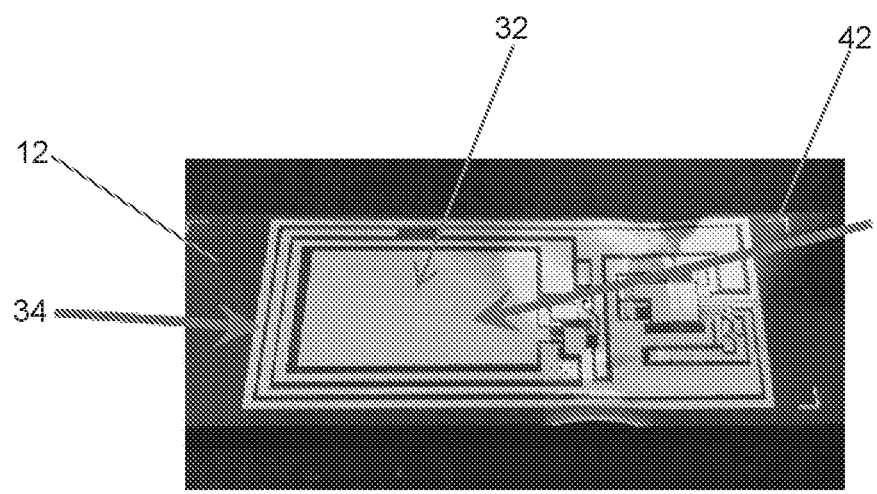
FIGS. 2(a) and 2(b) depict a top view (FIG. 2(a)) and a bottom view (FIG. 2(b)) of an inkjet printed circuit on Kapton tape according to the present disclosure.
Figure 2B:
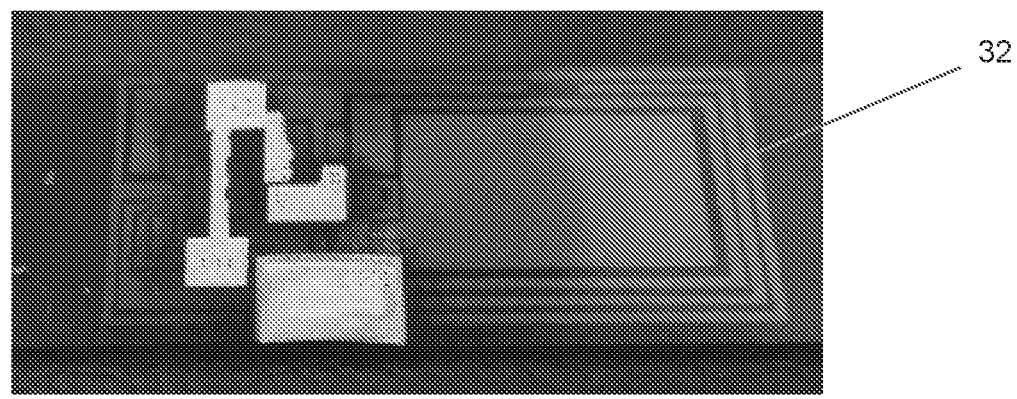
Figure 3:
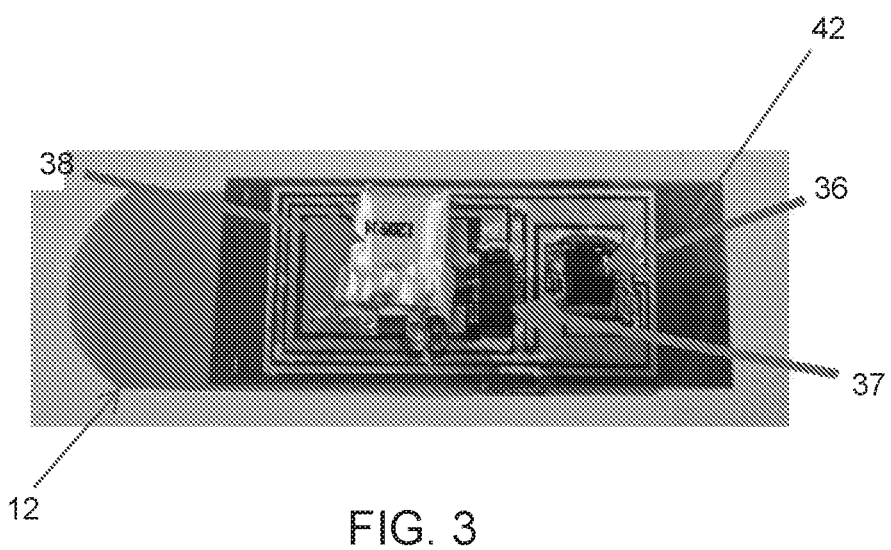
FIG. 3 depicts an embodiment of a complete smart bandage system.

A non-limiting embodiment of our wound dressing is depicted in FIGS. 1-3. The first part of the dressing 10 can be developed using commercially available dressing substrates such as bandage strips, for example, a strip 12 that may be 1 inch wide and 3 inches long, through the dressing substrate may have other dimensions. The bandage strip can serve as a substrate for one or more sensors, including a sensor electrode 22. A sensor electrode 22 can be printed on an element 14 for securing the sensor electrode 22 to the bandage substrate 12, for example on a simple adhesive tape. The sensor electrode 22 can be an interdigitated sensor electrode. In one or more aspects metal nanoparticles based ink, for example silver nanoparticles based ink, can be printed on the adhesive tape to form the sensor 22. The sensor electrode 22 can be mounted on the bottom side of the bandage substrate 12 as shown in FIG. 1(a) using the element 14, such as adhesive tape 14. A portion 24 of the electrode 22 can optionally be folded across the substrate or bandage strip 12, so that it is accessible to the top side 16 of the bandage strip 12 as shown in FIG. 1(b).

The second part, that comprises sensor electronics 32, can be provided using printing on adhesive tape, for example Kapton adhesive tape 42, as shown in FIG. 2(a). Again the printing can be carried out using an ink jet printer. A sensor circuit board as well as an antenna 34 and a top sensor electrode can be printed on the tape using, for example, silver nanoparticle ink. A two layer circuit board can be made on two sides of the tape. In order to make circuit interconnects on the bottom side of the tape, the adhesive can be selectively removed using, for example a laser. The laser can also be used to make via holes in the tape to connect the two layers of the circuit. An embodiment of a double sided circuit is shown in FIGS. 2(a) and 2(b). The circuit components can be mounted using, for example, silver epoxy paste. The components can include transceiver 36, for example a Zigbee transceiver chip (Texas instruments CC2530), a capacitance to digital converter (CDC) 37, (On Semiconductor LC717A00AJ), a battery 38, as shown for example in FIG. 3, and few passive components including a light emitting diode (LED) (not shown). The wireless signal frequency of the Zigbee standard can be around 2.4 GHz used for this application. The circuit can be attached to the bandage like a sticker to realize the complete system, as shown in FIG. 3.

The device or dressing 10 can detect bleeding from a patient's wound using a capacitive sensor formed by the two electrodes placed on the two sides of the bandage. The sensor can provide capacitive sensing of wounds conditions that can be monitored wirelessly.

The dressing device can function as follows. The dressing device can be placed on a patient's wound. In case the wound becomes active and exudes body fluid, the body fluid from the wound can penetrate into the dressing through the bottom sensor electrode. The body fluid will change the dielectric constant of the capacitor formed by the two electrodes that will change the capacitance between them. This capacitance change can be detected by the CDC 37 that activates the LED as well as the Zigbee transceiver 36. The LED can visually inform the patient about the status of the bandage, and the wireless transceiver 36 can send a signal to remote medical staff or health care provider informing them that the dressing needs to be changed. After use, the dressing part can be disposed-off whereas the electronic circuitry on Kapton can be peeled off and reused on another bandage.

A pH sensor can be incorporated in the device that can monitor the pH levels of the body fluid. These levels can help determine the condition of the wound and/or its healing status, and inform, for example, if the wound is getting infected. The body fluid can be blood. Also a blood glucose sensor can be added that can provide information about the blood sugar for diabetes monitoring.

Figure 4:
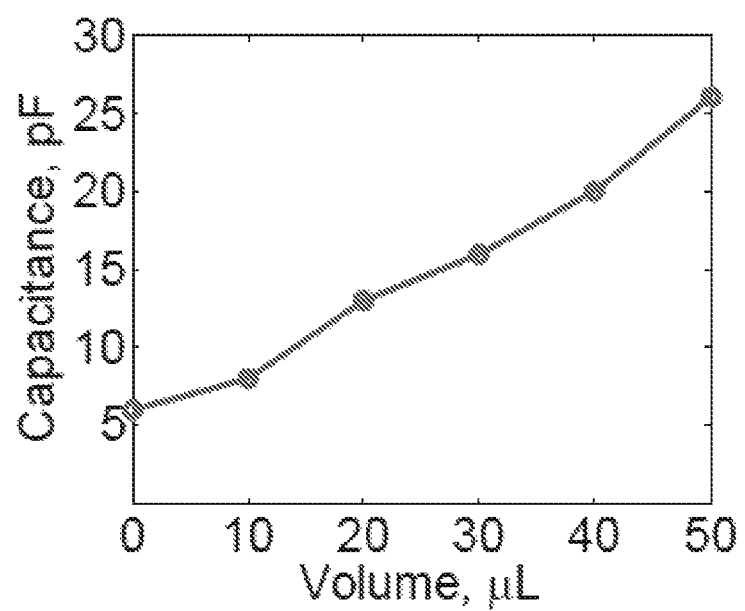
FIG. 4 depicts a characterization of a sensor of a wound dressing.

A prototype of the device was developed to detect bleeding from wounds, as shown in FIG. 1 to FIG. 3. The capacitive sensor was characterized, and the results are shown in FIG. 4. The results show that the sensor can detect blood volume levels of up to a few micro liters.

Example

We now provide the following example so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is in bar. Standard temperature and pressure, to the extend they may be referenced, are defined as 0° C. and 1 bar.

System Design and Operation

Figure 5:
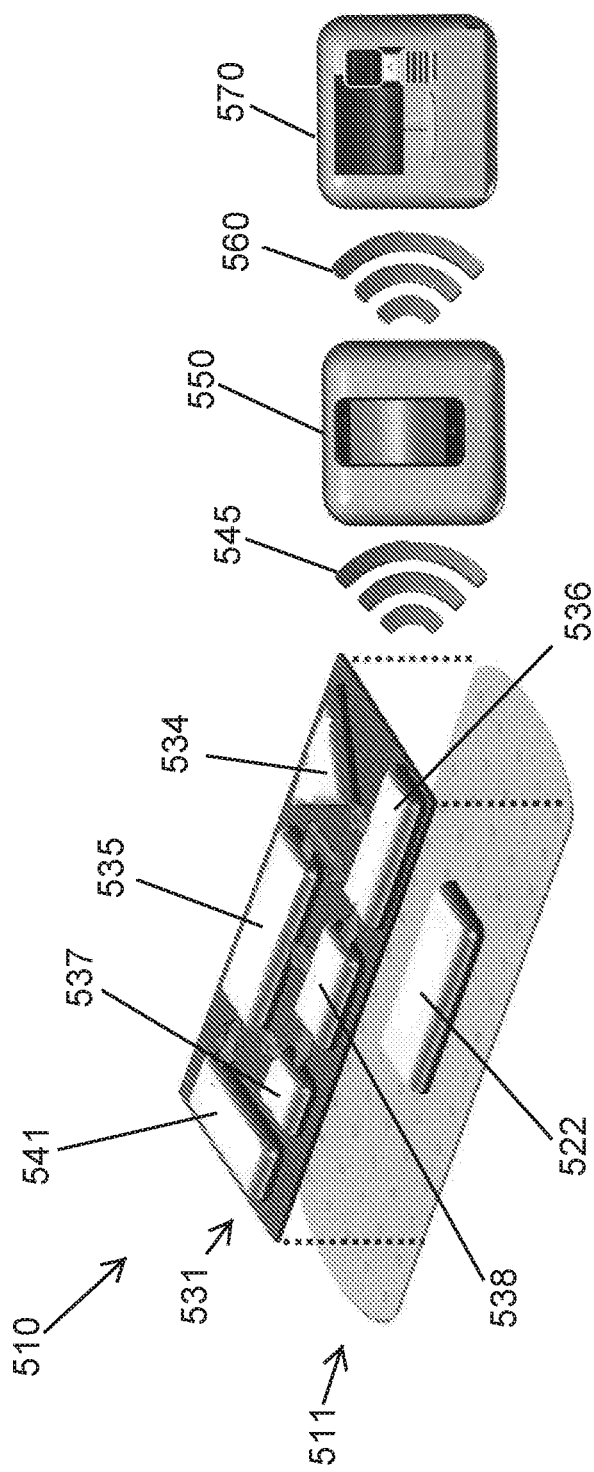
FIG. 5 depicts an example of a system design for our present disclosure.

An embodiment of a system level design of our present disclosure is depicted in FIG. 5. As mentioned above, the system 510 of the present example was designed as a combination of a disposable part (i.e., disposable bandage part) 511 and a reusable part 531 that can include detachable, reusable electronics to reduce the cost. The sensors 522 to detect bleeding, pH levels and external pressure on the wound are realized on a disposable bandage strip 512 whereas the electronics are integrated on a flexible substrate 542, such Kapton tape, which can be detached and reused multiple times.

Two types of sensing mechanisms or sensors 522 were used. A capacitive sensor detects bleeding as well as pressure levels on the wound. A resistive sensor detects the pH levels on the wound. The changes in capacitance and resistance are processed by the electronics and the information sent in a wireless fashion using IEEE 802.15.4 standard that operates around 2.4 GHz. The detachable electronics comprised a transmitter 536 with an embedded microcontroller or processing unit 535, a capacitance to digital converter (CDC) 537, an LED 539 to inform the patient about the status of the bandage and a battery 538 to power the system. The wireless communication is done through an antenna (such as an inkjet printed loop antenna) 534 that can be integrated with the circuit. The reusable part 531 can also include a voltage divider 541. The smart bandage system 510 can wirelessly communicate 545 with a personal smart phone 550 to provide wound progression data in a patient's personal environment. This data can then be sent from the patient's smart phone 550 to a remote monitoring device or system 570 to remote health care providers using either the mobile network or the internet 560.

The CDC 537 can continuously compare the sensor capacitance to a reference capacitance. When the sensor capacitance becomes greater than a reference capacitance as a result of bleeding or external pressure, the CDC 537 can output a signal, such as a logic high. This output can go into one of the ports of the microcontroller 535. The output from the resistive sensor is processed in a similar fashion to the capacitive sensor. The change in resistance of the sensor 522 is converted into voltage change which goes into another port of the microcontroller 535. The microcontroller 535 can continuously monitor the voltage level on these two ports and as soon as it detects a signal, it can activate the transmitter as well as the LED 539.

Sensor Design

Figure 6A:
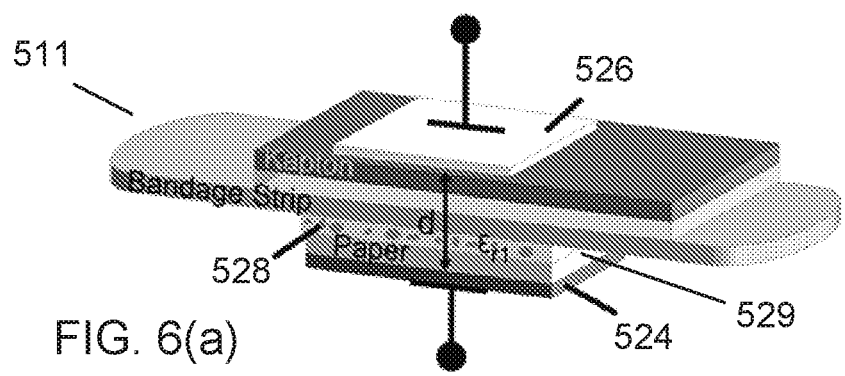
FIGS. 6(a)-(c) depict an example of a sensor design for our present disclosure.
Figure 6B:
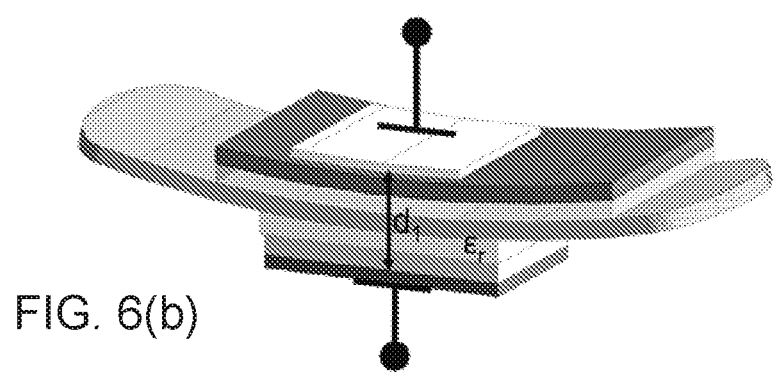
Figure 6C:
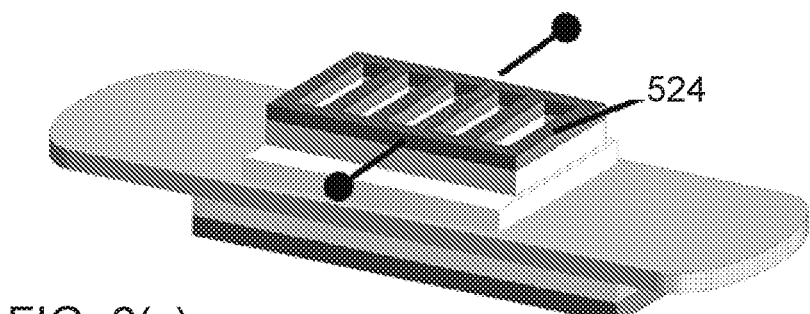

The smart bandage can sense various parameters related to chronic wounds which can be irregular bleeding, pH levels and external pressure. In order to sense these parameters, two types of sensing mechanisms were used, namely capacitive sensing and resistive sensing. These mechanisms are highlighted in FIGS. 6(a)-(c). As depicted therein, two sensor electrodes 524, 526 can be mounted on the bottom and the top side of the bandage strip 512 forming a capacitor. As depicted in FIG. 6(a), bleeding can be sensed when the blood 528 from the wound penetrates into the bandage pad 529 and changes the dielectric constant to $\varepsilon_{r1}$ which is greater than $\varepsilon_r$. As depicted in FIG. 6(b), the external pressure is sensed when the pressure changes the distance between the electrodes to $d_1$ which is less than d. The pH levels can be sensed when the resistance of bottom electrode (such as a carbon based electrode) changes in response to pH, as depicted in FIG. 6(c).

More particularly, a capacitor can be formed by placing the two electrodes 524, 526 on opposite sides of the bandage strip 512. The capacitance, C, of a metal-insulator-metal capacitor is given by $C=\varepsilon_0\varepsilon_r A/d$, where A is the area of the electrodes, d is the separation between the electrodes, $\varepsilon_r$ is the dielectric constant of the insulator between the electrodes and $\varepsilon_0$ is the permittivity of free space. The bleeding can be sensed due to the change in $\varepsilon_r$ of the capacitor. In the case that the wound starts to bleed, blood from the wound will penetrate into the bandage pad 529 and change the $\varepsilon_r$ of the bandage resulting in a change of capacitance. The external pressure can be sensed due to the change in d. When pressure is applied to the bandage, the two electrodes 524, 526 of the capacitor are pressed together and result in a smaller d. The change in d causes a change in capacitance. The pH levels on the wound site are detected by changes in resistance of one of the electrodes (carbon based) placed on the bandage.

The two electrodes 524, 526 were placed on the top and bottom side of the bandage. The bottom electrode can have a rectangle mesh geometry that has lines of width 1 mm and gaps of 2 mm as shown in FIG. 7(a). This geometry allows the blood to seep into bandage and also allows the bandage pad 529 to be in contact with the wound. In order to connect the bottom electrode 524 to the electronics at the top side of the bandage, part of this electrode 525 can be folded across the bandage so that it is accessible from the top as shown in FIG. 7(b). The top electrode 526 can be the form of a rectangular patch with dimensions of 14 mm×20 mm, and can be part of the detachable electronics as shown in FIG. 7(c). The two electrodes 524, 526 are therefore separated by the thickness of the bandage strip 511. The bottom electrode 524 can also form a resistive sensor in addition to being a part of the capacitive sensor. Since the bandage strip 511 has a limited area, this technique efficiently utilizes the area on the bandage by integrating two sensing mechanisms in one set of electrodes. The bottom electrode 524, as shown in FIG. 7(*a*), can be made using carbon based ink that is compatible with a screen printing process. When exposed to a solution containing hydronium ions ($H_3O^+$) in the case of an acid or hydroxide ions ($OH^-$) in the case of a base, the carbon can react with these ions which results in a change of its conductivity.

Antenna Design

A planar rectangular loop antenna 534 was designed for this Example. A loop antenna was chosen because of its planar design, differential operation and efficient area utilization. As shown in FIG. 7(*c*), the area inside of the loop can be utilized to place the electronics resulting in a compact design, since there is limited area on the bandage to place the sensor as well as the electronics. The loop antenna 534 was simulated in the presence of electronics located inside the loop to include the effect of the circuit on antenna performance. The simulations were carried out in Ansys HFSS. The results show that the antenna 534 radiates an omnidirectional pattern as expected and that the sensor electronics has little effect on the operation of the antenna. The antenna operates at around 2.4 GHz and has dimensions of 23.8 mm×46.5 mm. The maximum simulated gain of the antenna is around 0.5 dBi.

Printed Circuit Board on Kapton and System Integration

Conventional printed circuit boards (PCBs) are hard, bulky and rigid. The use of such PCBs for a wearable application is not suitable. In this work, a double-sided, detachable PCB was inkjet printed on Kapton adhesive tape 542 to keep the design light weight, flexible, conformal and comfortable for wearability as shown in FIGS. 7(*c*) and 7(*d*). The circuit can consist primarily of Texas Instruments® CC2530 transmitter chip and an ON Semiconductor® LC717A00AJ CDC chip with very few external components, which include an LED, a crystal resonator and a battery 538 as shown in FIG. 7(*e*). The transmitter 536 can includes an on-chip microcontroller to store the bleeding, pH and pressure data of the wound and can support data rates of up to 250 kbps which is well above the requirement for this particular application. The circuit was powered by a thin lithium-polymer battery 538 with dimensions of 2 mm×12 mm×12.5 mm. The thin (2 mm thick) battery from PowerStream Technology®, is light weight (0.45 gm.) and suitable for this design. If the bandage communicates after every 5 minutes in order to provide wound progression data, the battery 538 can operate the system 510 for up to 55 hours. The battery 538 can also be replaced or recharged using commercially available charging system by connecting them to the bandage. For this purpose, appropriate connections can be provided on the detachable electronics portion of the bandage. As mentioned above, the complete circuit is located inside the loop antenna 534 to optimize the space. A differential feed line connects the transmitter IC 536 to the antenna 534. The Kapton PCB tape 542 is shown in FIG. 7(*e*) after mounting of the components.

The circuit makes electrical contact with the bandage through pads 543 placed on the bottom side of the Kapton PCB tape 542. When the Kapton tape 542 is attached, these pads 543 connect to the folded portions 525 of the bottom electrode 524 on the bandage, which can be seen in FIG. 7(*b*). The use of inkjet printing to realize circuit board on Kapton tape makes the electronics detachable and reusable. The tape 542 can be attached to the bandage before it is worn by the patient as highlighted in FIG. 7(*f*). Finally, for simplicity the detachable electronics was covered from the top by another disposable bandage strip to demonstrate packaged smart bandage as shown in FIG. 7(*g*). Once used, the disposable bandage strip can be removed, as shown in FIG. 7(*h*), and the electronics can be reused on another bandage, which reduces the overall cost of the system.

Smart Bandage Fabrication

The bandage 510 can be fabricated using low cost inkjet printing process on flexible substrates. The fabrication of the bandage can take place in two parallel processes. The steps involved in these two processes are highlighted in FIGS. 8(*a*)-(*k*). The first process involves the fabrication of the bottom sensor electrode on paper substrate. Paper is one of the cheapest material and costs around one tenth of plastic[22]. It is flexible, biocompatible and biodegradable, thus it is extremely suitable for this application. Carbon ink is used for the metallization of bottom electrode. The second process involves the fabrication of sensor electronics as well as the top sensor electrode on Kapton tape, which is placed on the top of the bandage. Silver nanoparticle ink was used for the inkjet printing of top electrode, circuit board and antenna. After mounting of the components, the detachable sensor electronics as well as the bottom sensor electrode are attached to a disposable bandage strip. A commercially available adhesive bandage strip was used in this work which has a length of 3 in. and a width of 1 in.

More particularly, the bottom electrode fabrication can use carbon ink on paper, and the wireless electronics fabrication can use double-sided inkjet printed circuit board on Kapton. FIG. 8(*a*) shows the spreading of the carbon ink on a paper substrate. The bottom electrode can be cut using a laser, as show in FIG. 8(*b*). The bottom sensor electrode can be separated to form leads or connections for the bottom portion of the system, as shown in FIG. 8(*c*). The top removable portion of the system can be made by removing excess adhesive from a side of the Kapton tape, as shown in FIG. 8(*d*). FIG. 8(*e*) shows Inkjet printing of a circuit board on the bottom side of the Kapton tape and FIG. 8(*f*) shows Inkjet printing on the top side of the Kapton tape and thus on the side opposite the circuit board. The circuit components can be mounted, as show in FIG. 8(*g*), using silver epoxy. FIG. 8(*h*) shows the mounting of the bottom electrode and the integrated electronics on a disposable bandage strip. A bottom view of the assembled smart bandage system is shown in FIG. 8(*i*), and a top view of the assembled smart bandage system is shown in FIG. 8(*j*). Finally another disposable bandage strip can be put on top of the detachable electronics for packaging purpose, as shown in FIG. 8(*k*).

Bleeding and Pressure Sensing

The capacitive sensor placed across the bandage can sense bleeding. Blood has a dielectric constant of 58 at normal body temperature[23]. In order to mimic blood, a mixture of water and vegetable oil was made that has a similar dielectric constant as that of blood. Fixed volumes of this mixture were put on the bandage and the capacitance was measured across the two sensing electrodes. The capacitance is proportional to the dielectric constant between the electrodes.

As can be seen from FIG. 9(*a*), a few micro liters of fluid can make a significant change in capacitance. The initial capacitance value, $C_0$, of different samples varies from 2.4 pF to 2.7 pF which can be due to the slight misalignment of the top and bottom electrodes as they are placed manually. The variation in capacitance change as indicated by the errors bars can be due to the discrepancy in depositing the blood solution on the bandage. There is a possibility that small amount of solution stays on top of the bottom electrode which can prevent it from penetrating into the bandage.

Figures 9A, 9B:
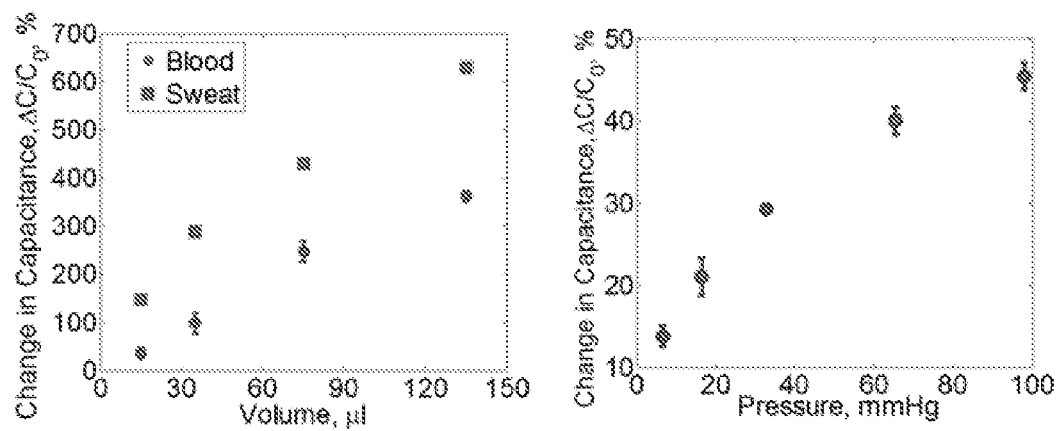
FIGS. 9(a) and 9(b) depict a characterization of a capacitive sensor of a wound dressing made in accordance with FIGS. 7(a)-(h) and FIGS. 8(a)-(k).

When a patient wears the bandage, other body fluids such as sweat and wound exudate can also seep into the bandage, which can result in an erroneous signal. An evaluation of capacitance change under influence of such body fluids was also carried out. Sweat and exudate are mostly water and contain electrolytes[24,25]. To mimic such fluids, a saline solution has been used. Similar volumes of saline solution and the blood mimicking mixture are put on the bandage and the capacitance change is measured. As can be seen in FIG. 9(a) there is a significant difference in the change of capacitance for saline and blood. Hence, by choosing an appropriate value for the threshold capacitor, the effect of body fluids can be minimized.

To measure external pressure using the capacitive sensor, different values of mass are put on the bandage in an area, A, of around 1 cm². The standard calibration weight set from Mettler Toledo® was used for this purpose. Masses, m, of 50 gm, 100 gm, 150 gm and 200 gm and 300 gm are put on the bandage. The pressure, P, corresponding to each mass is calculated using the relation P=(m*g)/A where g is the acceleration of gravity. The results are shown in FIG. 9(b). A pressure of around 6 mmHg produces a capacitance change of around 13%. Studies have shown that a pressure of more than 60 mmHg can result in muscle damage if applied for more than an hour[26,27]. The maximum variation in the capacitance change under external pressure is around ±2.3%.

pH Sensing

For pH measurements, solutions of acetic acid, water and ammonium hydroxide are used that provide acidic, neutral and basic pH solutions respectively. Pure acetic acid has a pH of 1.7, water has a pH of around 8 and ammonium hydroxide has a pH of around 12.9. One additional solution was prepared by diluting ammonium hydroxide that yields a pH of 10.9. The pH values were measured first using Hanna Instruments HI3222 pH meter. Line traces were made using manual screen printing of carbon ink that have an initial resistance, $R_0$. The traces are exposed to 10 μl of each of the pH solutions. The resistance changed immediately after exposure and takes some time to stabilize due to absorption of the solution.

Figure 10:
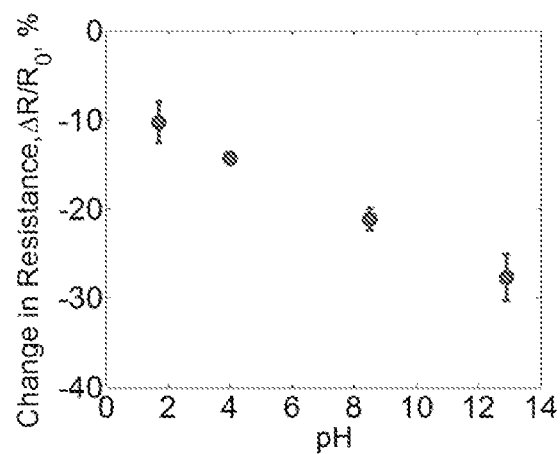
FIG. 10 depicts a characterization of a resistive sensor of a wound dressing made in accordance with FIGS. 7(a)-(h) and FIGS. 8(a)-(k).

The resistance was measured, and the results are shown in FIG. 10. It can be seen that the resistance decreases with increasing pH values. The change in the resistance of the carbon based electrode can be due to the adsorption of $OH^-$ and $H^+$ ions on the electrode surface. Carbon in this case is acting like a conductor with free electrons as the charge carriers. The adsorption of $H^+$ ions in the case of an acid result in the decrease in concentration of electrons on the surface of the electrode ($H^+$ being an electron acceptor). This causes a decrease in conductivity. The effect of $OH^-$ ions in the case of base is opposite, which result in the increased concentration of electron carriers and hence the conductivity. Similar behavior has been observed in the case of graphene[28-30] and carbon nanotubes[31]. The maximum variation in the resistance change due to pH is around ±2.6%. The pH values in chronic wounds vary between 5.4 to 8.6 according to one study[32]. In this range of pH, the variation in measurements is small.

System Tests

Figures 11A, 11B:
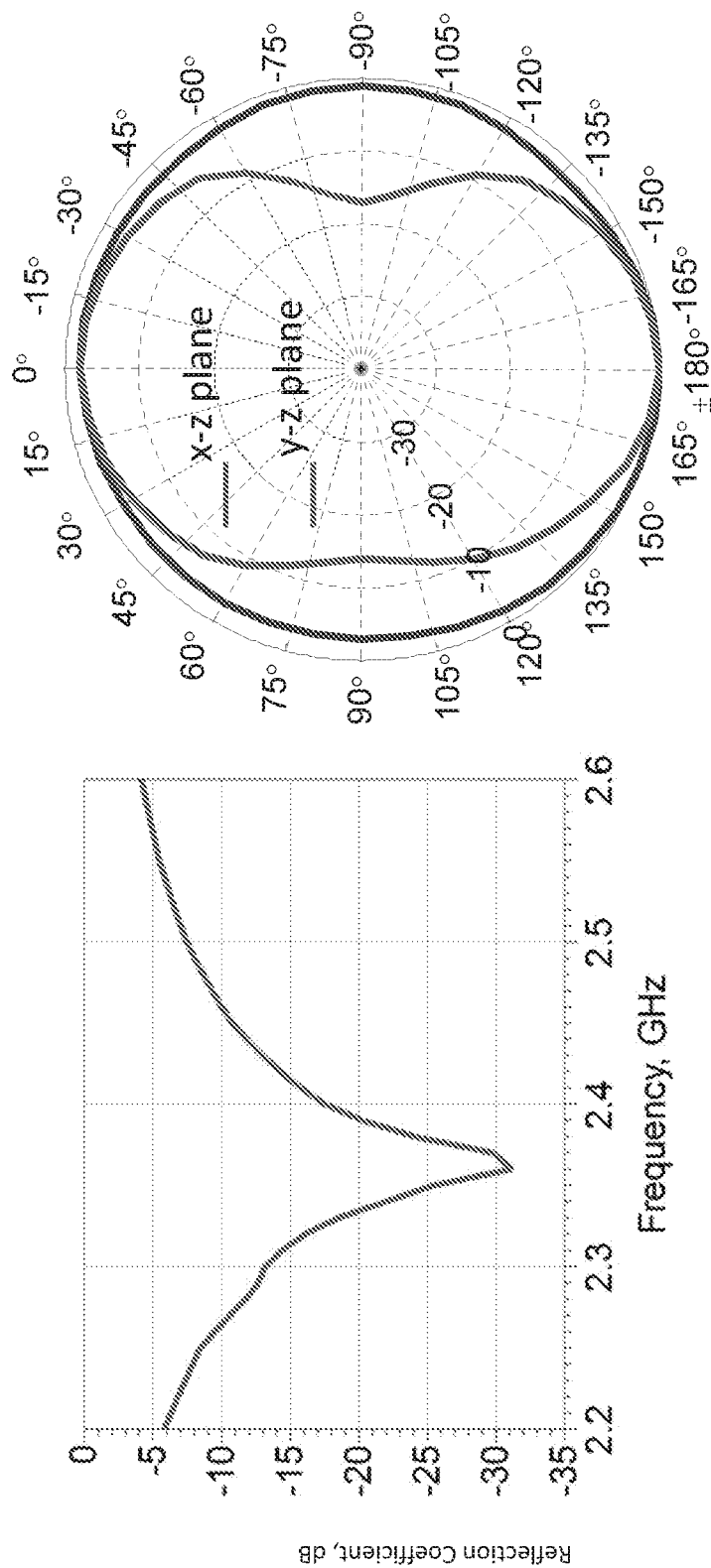

The system level measurements were performed that involve wireless tests of the bandage with electronics mounted. Firstly an active radiation pattern measurement of the antenna was measured. This was done as the antenna is surrounded by sensor electronics that may affect its radiation properties. The active pattern is shown in FIG. 11(b) along with the reflection coefficient of the antenna in FIG. 11(a).

As can be seen the active pattern is omnidirectional as expected from a loop antenna. Also the antenna is impedance matched at the operating frequency of 2.4 GHz.

Figure 12:
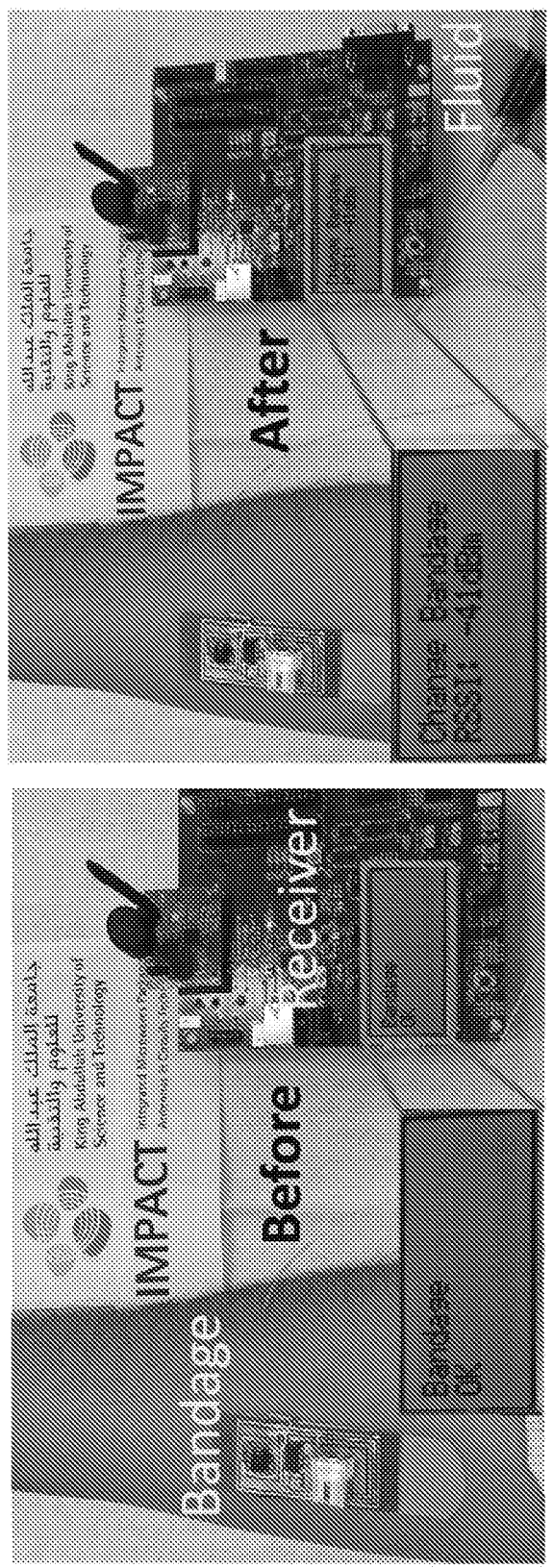
FIG. 12 illustrates an on-body setup of an embodiment of the present disclosure.

The wireless tests were performed while the bandage is worn on the body. To carry out the tests, a fluid is injected underneath the bandage using a narrow tube that is attached to a syringe containing the fluid. The setup is shown in FIG. 12. This setup is made to imitate bleeding from a wound. When there is no bleeding, the receiver displays 'Bandage OK' sign as shown in the left picture. When there is bleeding, which is modeled by injecting blood mimicking fluid underneath the bandage, the bandage communicates with the receiver that displays 'Change Bandage' sign as shown in the right picture. A Zigbee wireless receiver is placed to receive an information signal from the bandage. When the fluid is pumped from the syringe and reaches the bottom side of the bandage, the transmitter on the bandage is activated and sends information to the receiver.

Figure 13:
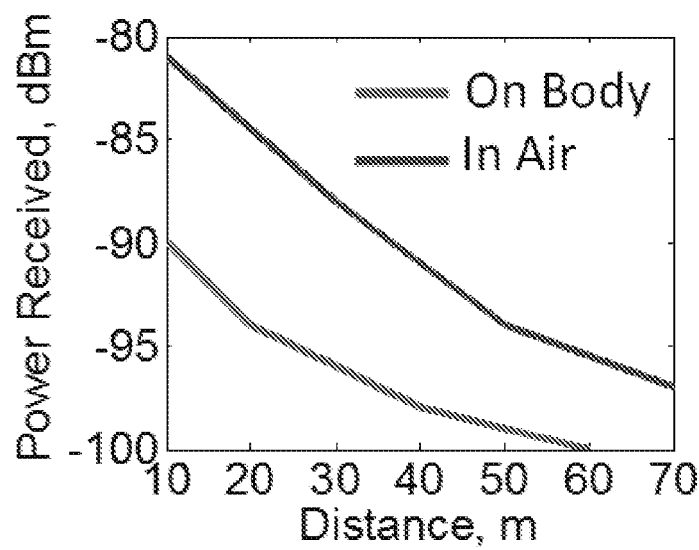
FIG. 13 shows the results of a range test for an embodiment of the present disclosure.

Field tests were carried out to measure the communication range of the bandage. The results are shown in FIG. 13. The range was measured with the bandage on a human body as well as in air. As can be seen from the results, a lower range of around 60 m is observed when the bandage is placed on a body as the proximity effects of the body change the radiation characteristics of the antenna. This shows the particular embodiment of the bandage can communicate to a receiver 60 m away when worn on the body. The deterioration in communication range is visible when the bandage is worn on the body as compared to when the bandage is in air due to the effects of body on the antenna performance.

Bending Response and Wearability Tests.

Figures 14A, 14B:
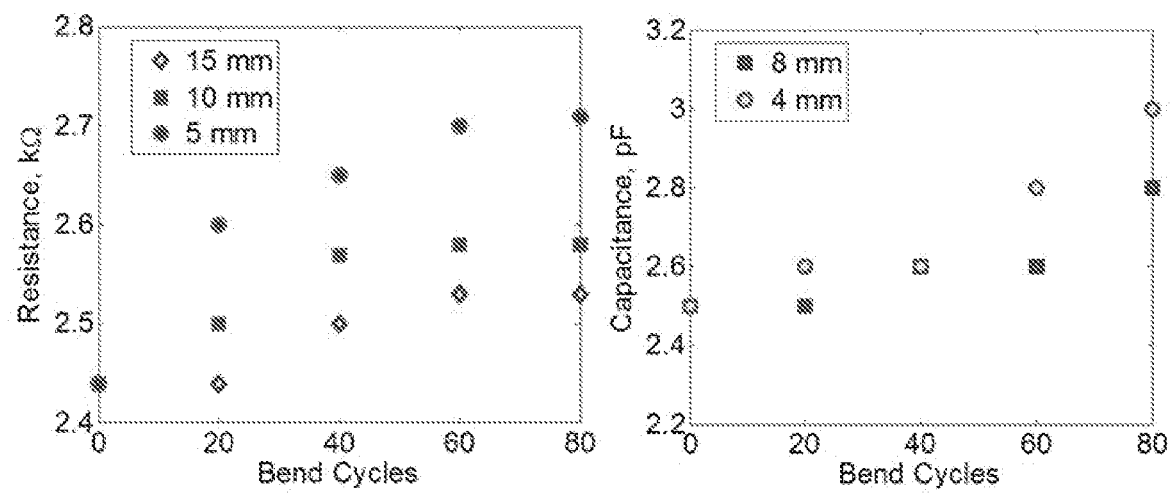
FIGS. 14 (a)-(b) show effects of bending on sensor characteristics, FIG. 14(a) showing the effect on the resistance of the resistive sensor and FIG. 14(b) showing the effect on the capacitance of the capacitive sensor after bending cycles of different radii.

Patients will wear the designed bandage, so we also evaluated the bandage performance in terms of flexibility and wearability. To perform flexibility tests, the bandage was subjected to several cycles of bending with different bending radii. The resistance of the bottom electrode and the capacitance across the bandage were measured after each bend cycle. FIG. 14a and FIG. 14b show the results. The resistance varies only slightly after the bending cycle. The capacitance value also does not change much with maximum variation of about 0.5 pF.

Figure 15A:
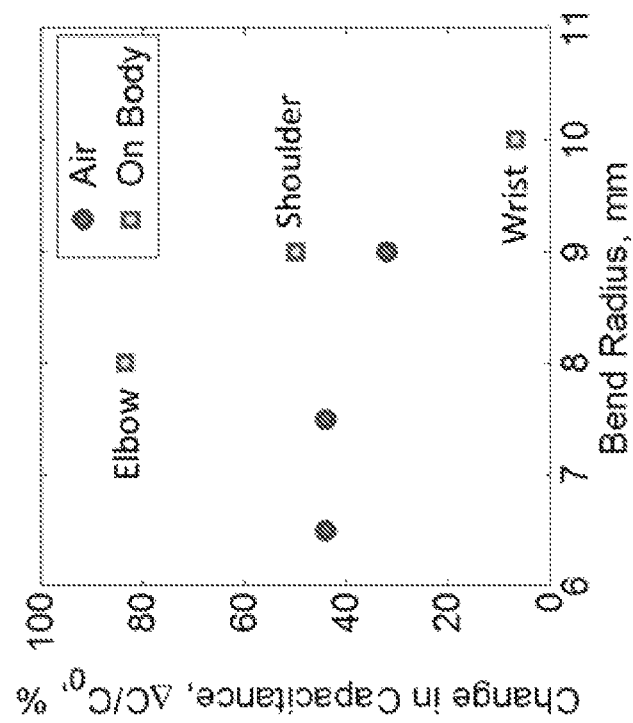
FIGS. 15(a)-(d) depict various wearability tests and results.
Figure 15B:
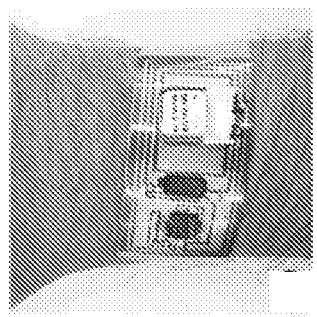
Figure 15C:
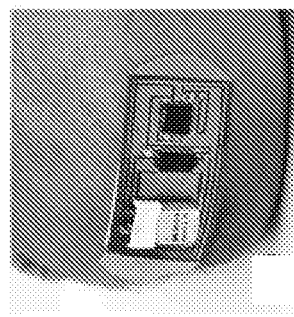
Figure 15D:
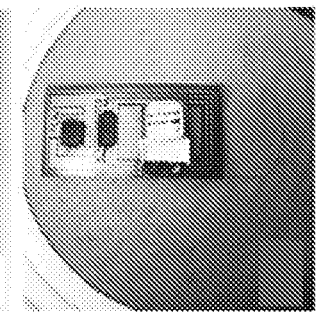

The capacitance of the sensor was also evaluated for different bending radii and also when worn on different body parts. The results are shown in FIGS. 15(a)-(d). The capacitance changes when the bandage is bent in air. A similar change in capacitance is observed when the bandage is worn on the body, as shown in FIG. 15(a). This can be due to the proximity effect of the body that can change the fringing field of the capacitive sensor. The bandage was also placed on the wrist, elbow and shoulder, as shown in FIGS. 15(b)-(d). The change in capacitance when worn on the wrist is minimal. The elbow and shoulder result in a bigger capacitance change due to the curvature of these joints. It can be noticed that once worn on the body, the variation in capacitance due to bending motion of different body parts is small as the variation in capacitance for different bend radii is small. This result is important for applications in everyday life as the patient wearing the smart bandage can move freely without affecting the operation of the bandage. The variation in capacitance, as shown in FIGS. 14(a)-(b), is much less than the capacitance change for blood and sweat samples as shown in FIG. 9a. Hence the bleeding can be clearly sensed even if there is any change in capacitance due to bending and an early warning can be issued.

Methods.
Fabrication

The bottom sensor electrode was made using carbon based ink manufactured by Bare Conductive®. The ink is compatible with screen printing process. The ink was spread on office paper using a squeegee in similar fashion to screen printing. The sheet resistance of the trace formed by the ink is around 90 Ω/square. A laser was used to cut the paper along the pattern of the electrode. The electrode is then attached on the bottom side of the bandage using glue. A portion of the electrode was folded across the bandage so that it can be accessed from the top by the sensor electronics.

The sensor electronics were fabricated on Kapton® tape as the substrate which has a thickness of 110 μm and width of 1 in. A double-sided printed circuit board was fabricated on the tape using inkjet printing. Silver nanoparticle based ink was used with an average particle size of 10 nm (UT Dots® Inc. UTDAgIJ1). The inkjet printing is done using a Dimatix® 2831 materials printer. Before printing, a laser is used to selectively remove the adhesive from the backside of the tape so that it becomes suitable for inkjet printing of the bottom side of the PCB. Also via holes were made using the laser to connect the two sides of the circuit. At this instance, the tape was cleaned with acetone to remove any contaminants. The circuit was inkjet printed with 80 um of drop spacing and 6 layers of ink. The tape was then put in an oven for sintering at 170° C. for 1 hour. The sheet resistance of the printed tracks on Kapton tape is around 0.4 Ω/square. After printing the circuit, the components were mounted using silver epoxy paste, as typical soldering is not feasible for inkjet printed tracks due to the high temperature of the soldering process which is around 280° C. The circuit was then attached to the bandage like a sticker in order to realize the complete system.

On Body Experiments

The bandage was worn by an adult human to assess the wearability as well as the performance of the bandage under bent condition at different body locations. The communication range was measured using Texas Instruments® SmartRF05 evaluation board and the resistance and capacitance was measured using Agilent® E4982A LCR meter while the bandage was in-situ. Informed consent was obtained from the human subject prior to the experiments. All experiments were performed in accordance with applicable guidelines and regulations, and the experimental protocol for on body testing was approved by KAUST Institutional Biosafety and Bioethics Committee (Approval #15IBEC34).

DISCUSSION

A new low cost smart wound dressing system that can sense multiple parameters for chronic wound monitoring is provided herein. The bandage can sense bleeding, pH levels and external pressure levels on the wound site providing important information for wound treatment, including chronic wound treatment. The bandage can communicate wirelessly to inform remote medical staff about the status of the wound as well as inform the patient about the need to change the bandage. The wound dressing system is shown to be suitable for wearability by a patient. The wound dressing system can use low cost materials, and cheap and simple fabrication process. The present system provides an attractive platform for integration of additional sensors for wound monitoring. These can include a temperature sensor and a humidity sensor as both of these parameters can play an important role in the wound healing process.

Mobile applications can also be linked to the smart bandage system and can provide the patient with hand-held capability to monitor the wound healing process. For example, for the case of a pressure ulcer, the external pressure on the wound site can be monitored by a patient's smart phone. The initial value of the sensor capacitance after wearing the bandage can be measured by the CDC and sent wirelessly to a patient's smart phone or to a monitoring station. In case an external pressure is applied on the wound, the resulting change in capacitance can also communicated. A smart phone application can then compute the change in capacitance with respect to the initial value and relate this change to the pressure levels based on the results shown in FIG. 9b. The smart phone can then alert the patient for repositioning in order to relieve the pressure. We, thus, provide a solution for low cost health care services to an ever increasing global population, that can reduce the burden on modern health care providers and government agencies.

Ratios, concentrations, amounts, and other numerical data may be expressed in a range format. It is to be understood that such a range format is used for convenience and brevity, and should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1% to about 5%, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figure of the numerical value. In addition, the phrase "about 'x' to 'y'" includes "about 'x' to about 'y'".

It should be emphasized that the above-described embodiments are merely examples of possible implementations. Many variations and modifications may be made to the above-described embodiments without departing from the principles of the present disclosure. All such modifications and variations are intended to be included herein within the scope of this disclosure and protected by the following claims.

REFERENCES

[1] Honda, W., Harada, S., Arie, T., Akita, S. & Takei, K. Wearable, human-interactive, health-monitoring wireless device fabricated by macroscale printing techniques. Adv. Funct. Mater. 24, 3299 (2014).

[2] Baig, M. M., Gholamhosseini, H. & Connolly, M. J. A comprehensive survey of wearable and wireless ECG monitoring systems for older adults. Med. Biol. Eng. Comput. 51, 485 (2013).

[3] Winokur, E. S., Delano, M. K. & Sodini, C. G. A wearable cardiac monitor for long-term data acquisition and analysis. IEEE Trans. Biomedical Engg. 60, 189 (2013).

[4] Zheng, Y-L., Yan, B. P., Zhang, Y.-T. & Poon, C. C. Y. An armband wearable device for overnight and cuff-less blood pressure measurement. IEEE Trans. Biomedical Engg. 61, 2179 (2014).

[5] Mihajlovic, V., Grundlehner, B., Vullers, R. & Penders, J. Wearable, wireless EEG solutions in daily life applications: What are we missing? IEEE J. Biomedical Health Informatics 19, 6 (2015).

[6] Sen, C. K. et al. Human skin wounds: A major and snow balling threat to public health and economy. Wound Repair Regen. 17, 763 (2009).
[7] Posnett, J., Gottrup, F., Lundgren, H. & Saal, G. The resource impact of wounds on health-care providers in Europe. J. Wound Care 18, 154 (2009).
[8] Nunan, R., Harding, K. G. & Martin, P. Clinical challenges of chronic wounds: searching for an optimal animal model to recapitulate their complexity. Disease Models & Mechanisms, 2014, 7, 1205.
[9] Blakytny R. & Jude, R. E. The molecular biology of chronic wounds and delayed healing in diabetes. Diabet. Med. 6, 594 (2006).
[10] Gist, S., Matos, I. T., Falzgraf, S., Cameron, S. & Beebe, M. Wound care in the geriatric client. Clin. Interv. Aging. 4, 269 (2009).
[11] Gardner, S. E., Frantz, R. A. & Doebbeling, B. N. The validity of the clinical signs and symptoms used to identify localized chronic infection. Wound Repair and Regeneration 9, 178 (2001).
[12] Hampton, S. Understanding overgranulation in tissue viability practice. British Journal of Community Nursing 12, 9 (2007).
[13] Schreml, S., Szeimies, R-M, Karrer, S., Heinlin, J., Landthaler, M. & Babilas, P. The impact of the pH value on skin integrity and cutaneous wound healing. J. European Academy Dermatology Venereology 24, 373 (2010).
[14] Dharmarajan, T. S. & Ugalino, J. T. Pressure ulcers: Clinical features and management. Hospital Physician 38, 64 (2002).
[15] Li, Z. et al. Non-invasive transdermal two-dimensional mapping of cutaneous oxygenation with a rapid drying liquid bandage. Biomedical Optics Express 5, 3748 (2014).
[16] Guinovart, T., Ramirez, G. V-., Windmiller, J. R., Andrade, F. J. & Wang, J. Bandage-based wearable potentiometric sensor for monitoring wound pH. Electroanalysis 26, 1345 (2014).
[17] Swisher, S. L. et al. Impedance sensing device enables early detection of pressure ulcers in vivo. Nature Commun. 6, 6575 (2015).
[18] M. J. Farrow, I. S. Hunter and P. Connolly, "Developing a Real Time Sensing System to Monitor Bacteria in Wound Dressings," Biosensors 2, 2012, 171-188.
[19] D. McColl, B. Cartlidge, P. Connolly, "Real-time monitoring of moisture levels in wound dressings in vitro: An experimental study," International Journal of Surgery (2007) 5, 316-322.
[20] V. Sridhar, K. Takahata, "A hydrogel-based passive wireless sensor using a flex-circuit inductive transducer," Sensors and Actuators A 155 (2009) 58-65.
[21] N. Mehmood, A. Hariz, S. Templeton and N. H. Voelcker, "An Improved Flexible Telemetry System to Autonomously Monitor Sub-Bandage Pressure and Wound Moisture," Sensors, 14, 2014, 21770.
[22] Steckl, A. J. Circuits on cellulose. IEEE Spectrum 50, 48-61(2013).
[23] Cook, H. F. A comparison of the dielectric behavior of pure water and human blood at microwave frequencies. British Journal of Applied Physics 3, 249 (1952).
[24] Cutting K. Wound exudate: composition and functions. Br J Community Nurs. 2003; 8(9 Suppl):4-9.
[25] Harvey, C. J., LeBouf, R. F. & Stefaniak, A. B. Formulation and stability of a novel artificial human sweat under conditions of storage and use. Toxicology in Vitro 24, 1790 (2010).
[26] Patterson, J. A. & Bennett R. G. Prevention and treatment of pressure sores. J Am. Geriatr. Soc. 43, 919 (1995).
[27] Witkowski J. A. & Parish L. C. Histopathology of the decubitus ulcer. J. Am. Acad. Dermatol. 6, 1014 (1982).
[28] Lei, N., Li, P., Xue W. & Xu, J. Simple graphene chemiresistors as pH sensors: fabrication and characterization. Meas. Sci. Technol. 22, 107002 (2011)
[29] Ang, P. K., Chen, W., Wee, A. T. S. & Loh, K. P. Solution-gated epitaxial graphene as pH sensor. J. Am. Chem. Soc. 130, 14392 (2008).
[30] Ohno, Y., Maehashi, K., Yamashiro, Y. & Matsumoto, K. Electrolyte-gated graphene field-effect transistors for detecting pH and protein adsorption. Nano Lett. 9, 3318 (2009).
[31] D. Jung, M.-E. Han, G. S. Lee, "pH-sensing characteristics of multi-walled carbon nanotube sheet," Materials Letters 116 (2014) 57-60.
[32] Percival S. L., McCarty S., Hunt J. A., Woods E. J. The effects of pH on wound healing, biofilms, and antimicrobial efficacy. Wound Rep. Reg. 22, 174 (2014)

Therefore, the following is claimed:

1. A wound dressing system comprising:
a disposable substrate portion, which includes a first substrate, a first electrode of a sensor and a bandage pad interposed between a first side of the first substrate and the first electrode; and
a reusable portion, which includes a flexible substrate having a first side removably coupled to a second side of the first substrate, wherein sensor electronics and a second electrode of the sensor are arranged on a second side of the flexible substrate and the second electrode is electrically coupled to the sensor electronics.

2. The wound dressing system of claim 1, wherein the first electrode of the sensor is configured to allow bodily fluids to pass through it to the bandage pad.

3. The wound dressing system of claim 1, wherein the first and second electrodes form a capacitive sensor.

4. The wound dressing system of claim 3, wherein the capacitive sensor senses bodily fluids.

5. The wound dressing system of claim 4, wherein the capacitive sensor senses pressure applied to the wound dressing system.

6. The wound dressing system of claim 1, wherein the first electrode is coupled to the sensor electronics to form a resistive sensor.

7. The wound dressing system of claim 1, further comprising:
an antenna arranged on the flexible substrate and coupled to the sensor electronics.

8. The wound dressing system of claim 7, wherein the antenna is a loop antenna and the sensor electronics are arranged inside of the loop antenna.

9. The wound dressing system of claim 1, wherein the flexible substrate is an adhesive tape.

10. The wound dressing system of claim 1, wherein the sensor electronics comprise:
a wireless transmitter; and
a capacitance to digital converter coupled to the first and second electrodes and to the wireless transmitter.

11. The wound dressing system of claim 10, wherein the wireless transmitter includes a microcontroller configured to store readings from the sensor.

12. A method of making a wound dressing system, the method comprising:
arranging a first electrode of a sensor on a first side of a bandage pad, and arranging a second side of the bandage pad on a first side of a first substrate;
arranging sensor electronics and a second electrode on a first side of a flexible substrate; and
removably coupling a second side of the flexible substrate with a second side of the first substrate, wherein the step of removably coupling the flexible substrate and the first substrate electrically couples the first electrode with the sensor electronics.

13. The method of making a wound dressing system of claim 12, further comprising:
arranging a loop antenna on the first side of the flexible substrate and surrounding the sensor electronics.

14. The method of making a wound dressing system of claim 12, wherein the arranging of the first electrode of the sensor further comprises arranging a portion of the first electrode on the second side of the first substrate so that the first electrode is electrically coupled to the sensor electronics when the flexible substrate and the first substrate are removably coupled.

15. The method of making a wound dressing system of claim 12, wherein the sensor electronics include a wireless transmitter and a capacitance to digital converter, the method further comprising:
electrically coupling the capacitance to digital converter to the first and second electrodes; and
electrically coupling the capacitance to digital converter to the wireless transmitter.

16. A wound dressing system, comprising:
a disposable portion, which includes: a bandage pad positioned between a first electrode and a first side of a first substrate;
a reusable portion, which includes: sensor electronics and a second electrode arranged on a first side of a flexible substrate, wherein a second side of the flexible substrate is removably coupled to a second side of the first substrate;
a capacitive sensor coupled to the sensor electronics; and
a resistive sensor coupled to the sensor electronics,
wherein the capacitive sensor comprises the first electrode, the first electrode being arranged on the bandage pad, and the second electrode arranged on the reusable portion so that the bandage pad is interposed between the first electrode and the second electrode, and
wherein the resistive sensor comprises the first electrode.

17. The wound dressing system of claim 16, wherein the first electrode is configured to allow bodily fluids to pass through it to the bandage pad.

18. The wound dressing system of claim 16, further comprising:
an antenna arranged on the flexible substrate of the reusable portion and the antenna is coupled to the sensor electronics.

19. The wound dressing system of claim 18, wherein the antenna is a loop antenna and the sensor electronics are arranged inside of the loop antenna.

20. The wound dressing system of claim 16, wherein the sensor electronics comprise:
a wireless transmitter, which includes a microcontroller configured to store readings from the capacitive and resistive sensors; and
a capacitance to digital converter coupled to the first and second electrodes and to the wireless transmitter.

* * * * *